United States Patent [19]

Wylie et al.

[11] Patent Number: 5,083,742
[45] Date of Patent: Jan. 28, 1992

[54] FLUID CONTROL VALVE

[75] Inventors: David A. Wylie, Unionville; Richard C. Leveson, Willowdale; Paul C. P. Thomson, Weston; Donald S. N. Bray, Toronto, all of Canada

[73] Assignee: Photovac Incorporated, Thornhill, Canada

[21] Appl. No.: 561,103

[22] Filed: Aug. 1, 1990

[51] Int. Cl.[5] .................................... F16K 31/126
[52] U.S. Cl. ................................ 251/61.1; 137/883; 137/885; 251/368
[58] Field of Search ........... 73/863.71, 863.72, 863.73; 92/103 M; 137/863, 883, 885; 251/61.1, 368

[56] References Cited

U.S. PATENT DOCUMENTS

| | | | |
|---|---|---|---|
| 3,057,376 | 10/1962 | Agutter et al. | 251/61.1 |
| 3,123,096 | 3/1964 | Notaro et al. | 251/368 |
| 3,130,954 | 4/1964 | McFarland | 251/368 |
| 3,312,238 | 4/1967 | Voit | 251/61.1 |
| 4,037,622 | 7/1977 | Osheroff et al. | 251/61.1 X |
| 4,070,004 | 1/1978 | Friswell | 251/368 X |
| 4,119,120 | 10/1978 | Mehaffy et al. | 137/885 |
| 4,353,243 | 10/1982 | Martin | 251/61.1 X |
| 4,703,913 | 11/1987 | Hunkapiller | 251/61.1 |
| 4,869,282 | 9/1989 | Sittler et al. | 251/61.1 |

Primary Examiner—Gerald A. Michalsky
Attorney, Agent, or Firm—Skjerven, Morrill, MacPherson, Franklin & Friel

[57] ABSTRACT

A fluid flow control valve for use with chemical fluids where avoidance of contaminants is important, is provided. The valve has a flow control chamber divided into an analytical section and a driver section by a metallic foil membrane operating member, clamped between the peripheral rim of the chamber and the upper wall. The foil membrane is moveable in response to driver fluid pressure between open and closed positions. The upper portion of the rim which engages the membrane is of relatively small surface area, and is made of a softer material than that from which the membrane and the upper wall are constructed, thereby providing a very effective means of sealing the membrane periphery to the upper wall when tightly clamped. The membrane is of domed shape, and is formed in situ by deformation of a planar metal foil sealingly clamped in position within the chamber, by application of fluid pressure thereto through a port to the chamber.

20 Claims, 9 Drawing Sheets

FLUID CONTROL VALVE

FIELD OF THE INVENTION

This invention relates to fluid flow control valves, and particularly to the type of fluid flow control valve in which the flowing fluid is controlled by a metallic flexible control member, so that the fluid only contacts inert metal surfaces as it passes through the valve.

BACKGROUND OF THE INVENTION

There are many situations in industrial and analytical chemistry where a flowing stream of chemical fluid needs to be controlled, in a manner in which the risk of contamination of the flowing stream by contact with surfaces must be minimized. Examples include automatic flow monitoring systems and meters, analytical apparatus, gas chromatography, medical gas supply lines and the like. In such cases, it is necessary to provide flow control valves in which all the surfaces which contact the flowing chemical fluid, including the valve operating member, are constructed or at least have surfaces covered with inert metal. In many of these cases also, particularly in the case of flow control valves for use with analytical apparatus, very small size valves of high precision are required, to handle analysis of flowing fluids with precision capable of detection and analysis of fluid contaminants of the order of a few parts per billion.

Specific examples of such applications are high performance liquid chromatography (HPLC) and gas chromatography. In both of these applications, small scale, high precision fluid flow control valves are needed. Especially in gas chromatography, where small amounts of contaminants are required to be detected and analyzed, it is necessary to have a flow control valve which presents chemically inert surfaces to the gas flow.

Gas chromatography is a technique by which a mixture of chemical compounds which are in the gaseous or vaporous state are separated from each other by passing them through a column in which they come into contact with an absorptive medium. A stream of gas (known as the carrier gas) passes through the column to provide transport for the chemical compound through the column. Each chemical species has a different level of affinity to be absorbed and will pass through the column in a time which is in proportion to that affinity. In this manner, compounds emerge from the column separated in time.

In modern gas chromatography, it is often necessary to control more than one stream of carrier gas at the same time and to carry out precisely timed switching of streams of gas. To accomplish this, a number of highly specialized valves are needed. It is important that the valves be made of a chemically inert material for which the chemical compounds under analysis have very low affinity and to which they do not readily diffuse. It is also important that internal volume within a gas chromatography system should be kept to a minimum. This in turn means that the fluid flow control valves must have low internal volume (dead volume), in order to provide the necessary degree of sensitivity.

BRIEF REFERENCE TO THE PRIOR ART

It is known to provide metal foil membranes or diaphragms as operating members in valves for gas chromatography. Metallic foil membranes can be made of highly inert metals, to minimize contamination of the components of the gas mixture therewith. Metal foils will also withstand high temperatures of operation. For example, U.S. Pat. No. 4,353,243 Martin shows a multiport flexible diaphragm control valve for use with chromatography systems, which can use a thin metallic sheet as its diaphragm, operable by fluid pressures applied to the lower side of the diaphragm to move it between positions opening and closing communication between ports located on the upper side of the diaphragm.

U.S. Pat. No. 4,869,282, Sittler et al discloses a micro machined miniature valve for gas chromatography, in which a metal foil diaphragm film can be used, the diaphragm being operated in response to fluid pressure.

U.S. Pat. No. 3,057,376 Agutter et al shows a fluid operated valve suitable for use in gas chromatography, having a combination of stacked plates, some having ports, defining a passageway to conduct fluids. Air pressure is used to compress a flexible plate sandwiched between rigid plates, against a port to close the valve. This flexible plate can be a flexible metal sheet.

In these miniaturized valves for use with gas chromatography apparatus, it is essential that an effective seal be provided by the diaphragm, not only to close the respective ports when required, quickly and efficiently, but also to prevent leakage of gases out of the valve chambers around the edges of the diaphragm. Any leakages of this nature will interfere with the accuracy of the analytical results to be obtained. In many instances, the operator is seeking analytical results of the order of a few parts per billion, or even less, of a compound in a gas stream, so that it is essential to provide adequate seals and operating efficiency of the valves.

The adequate sealing of flat metal members such as plates and foils against one another, however, presents considerable difficulties. Irregularities in the metal surfaces cannot be tolerated. The problem is particularly acute where multiple valves of such small size are provided on one metal block, since leakage around such irregularities will give inaccurate chromatographic results and could lead to cross contamination of fluid streams.

The provision of metal operating members, as opposed to rubber, plastic or other, more easily sealable substances, is highly desirable, despite the sealing problems attendant upon the use of such metal foils. Non-metallic materials will often exude organic materials. Moreover, they tend to absorb organic fluids from the flowing stream during one analytical operation, and to release them into the flowing stream of another, subsequent analytical operation. The quantities of such absorbed and re-released materials may be very small, but can be sufficient to distort gas chromatography analytical results, especially in cases where a high concentration organic mixture analysis is followed by a very low concentration mixture analysis.

SUMMARY OF THE INVENTION

It is an object of the present invention to provide a novel valve design for use in controlling fluid flows where it is important to avoid chemical contamination of the fluid.

It is a further object of the present invention to provide such a valve design which utilizes a metal foil as the operating diaphragm, and adequately seals the all-metallic surfaces of the valve chamber against leakage.

It is a further object of the invention to provide such a valve design which operates quickly and efficiently, with fast response times.

It is a further object of the invention to provide a process for making such valve designs, with the necessary high degree of precision.

The valve design of the present invention includes a metal foil diaphragm or membrane clamped within a valve chamber, between the upper wall and the upper surface of the side rim of the chamber, effectively dividing the chamber into a driver side, from which the valve is pneumatically or hydraulically operated, and an analytical side through which the fluid flows. The membrane is of generally domed configuration. Inlet and outlet ports extend into the analytical side through the upper wall. The membrane is operated by fluid pressure applied through a passageway into the driver side, to seal off the inlet and outlet ports as required. In order to effect the adequate sealing of the foil membrane within the chamber, the membrane-engaging surface of the upper extremity of the side rim is of smaller surface area than the surface area of the upper wall of the valve chamber, and the membrane engaging portion of the side rim is made of a softer material than that from which the foil membrane itself is made, and that from which the upper wall is made.

With this combination of features, a valve can be made which will operate accurately and precisely, over a very extended number of cycles of operation (in excess of one million), whilst maintaining the necessary seal against escape of the flowing fluids from the valve chamber. Moreover, this combination of features allows the membrane to be assembled in the chamber and then formed into its domed shape in situ by application of fluid pressure to the analytical side of the chamber.

According to another aspect of the invention, there is provided a process for constructing a flow control valve of this type, which has a metallic foil membrane operating member. In the process, the metallic foil is initially provided in planar form, and clamped in position in the chamber, between the upper extremity of the rim and the upper wall. Then it is deformed in situ in the chamber, to its domed shaped, by application of fluid pressure to the analytical side of the chamber. In this manner, the membrane is deformed into its domed shape in close conformity to the walls and the contours of the driver side of the valve chamber itself, to provide for efficient operation thereof. The arrangement of small surface area of the top of the rim where the membrane is clamped, and the relative hardness and softness of the foil membrane engaging surfaces as described above, allows this in situ formation to proceed efficiently and quickly, to provide a valve design ready for use.

BRIEF REFERENCE TO THE DRAWINGS

FIG. 1 of the accompanying drawings is a diagrammatic cross sectional view of a valve design according to the specific preferred embodiment of the present invention, with the depth of the valve chamber exaggerated for illustrative purposes;

DESCRIPTION OF THE PREFERRED EMBODIMENTS

Figure 1:
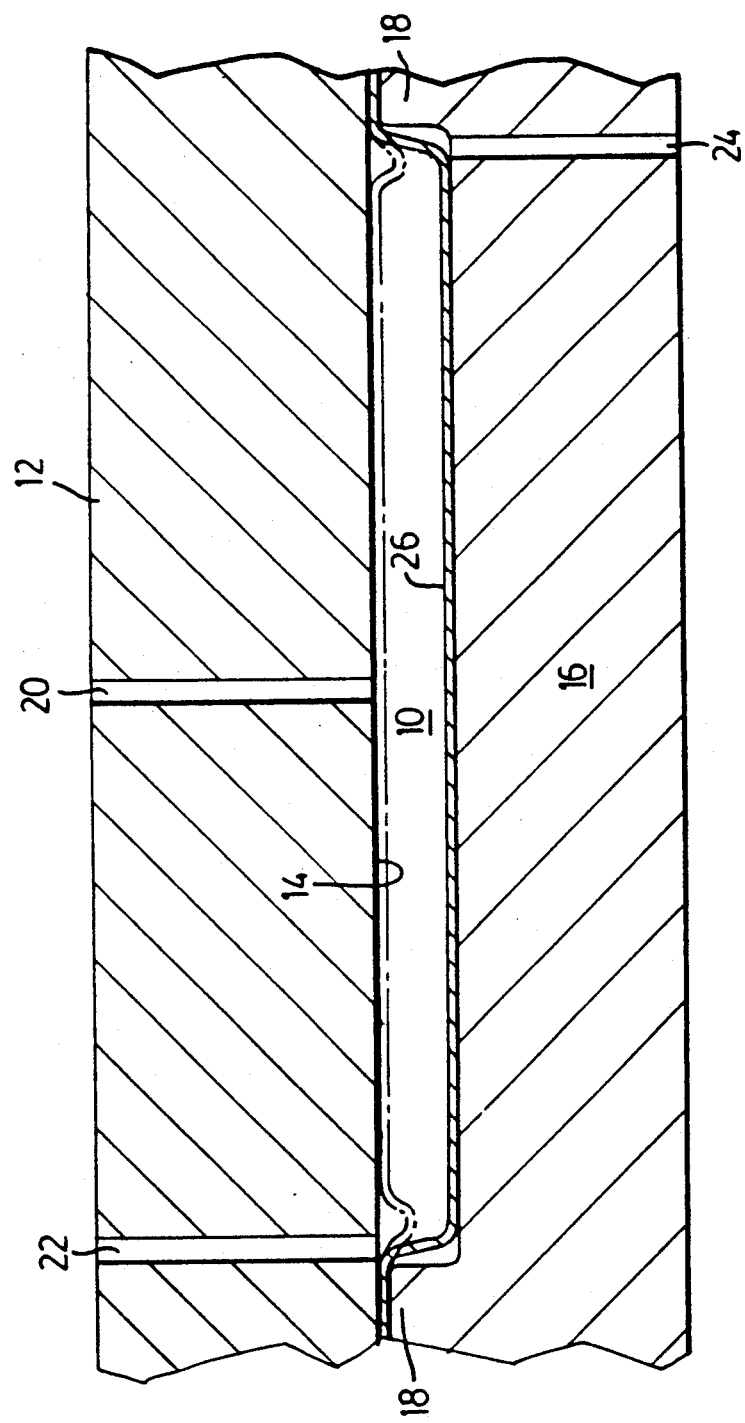
FIGS. 1A, 1B and 1C illustrate alternative arrangements similar to the one illustrated in FIG. 1.

The valve design of the present invention is preferably arranged with a common inlet which links two chambers. Each of the valve chambers is preferably circular as viewed in plan, and is provided with a single, common foil sheet extending across both chambers, on which the dome shapes are formed in each of the two chambers. Each chamber has a single driver fluid passageway into the driver side to operate the membrane. The upper wall of each chamber is preferably provided with a single fluid inlet port and a single outlet port, the inlet ports from a pair of chambers being connected together. In action, the two chambers act as a fluid "switch", the outlet from one chamber being held closed while the other is open, and vice versa. In addition, the linked pair of valves can be used to mix two separate fluid streams by connecting the gas streams to the ports held closed by the membrane domes, and opening both domes simultaneously. Pairs of valves, according to the invention can be built into arrays, each pair acting as a valve to direct fluid flow in one or another direction for a series of analytical procedures.

Suitable materials for the manufacture of the foil membrane include stainless steel and cobalt chromium-nickel alloys, and other metallic materials with high tensile strength. They are available on the market. One specific suitable such membrane material is that sold under the trademark HAVAR by Hamilton Precision Metals, Lancaster, Pennsylvania. It is a cobalt-nickel-chromium alloy foil of thickness 0.0005 inch. It can be used as purchased, after cleaning and cutting to the correct shape and size. Such a membrane is inert towards the gases to be analyzed, and can withstand very high temperatures so that the apparatus can be operated at high temperatures if desired. It possesses the high tensile strength required for high pressure deformation according to the process of the present invention, and, due to its high tensile strength, it is capable of withstanding millions of repeated cycles of operation.

In another alternative embodiment, such a membrane material is provided with an upper surface coating of noble metal such as gold or platinum, further to enhance the inertness thereof towards the analytical gases. Such a coating is suitably applied by a plating or sputtering process to either or both of the membrane surfaces, and suitably also to the underside of the top wall where it will contact the gas to be analyzed. In addition to the desired inertness provided by such noble metal coatings, they may assist in protecting the membranes from the effects of mechanical wear, on repeated operation of the membrane as a valve member.

Suitable materials for use in constructing the upper wall of the chamber walls are stainless steel, nickel plated metals such as aluminum, plastic resin plated with an inert metal such as nickel, or inert ceramic material which may also be similarly plated. The material should be capable of being produced with or polished to a very smooth surface finish, so as to provide for appropriate fluid tight sealing with the foil membrane.

As noted, the foil engaging portions of the rims of the chambers are constructed of a material which is softer than the material of the foil, and softer than the material of the top wall of the chamber. Examples of such materials, when stainless steel is used for the upper wall and stainless steel or HAVAR for the membrane, are brass and copper. When a hard plastic resin is used for the top wall, a softer plastic resin may be used for the membrane-engaging portion of the rims of the chambers. The entire bottom wall structure and rim of the chamber may be made of the same softer material. Alternatively, only the rims, or only the upper portion of the rims, may be made of this softer material. Any of these arrangements, in combination with the small surface area of the membrane-engaging surface of the rims, provides the necessary effective seal in accordance with the present invention. The choice between these various designs can conveniently be made on the basis of the ease of manufacture of the specific designs.

In this arrangement of harder and softer surfaces according to the invention, any plastic flow or yielding of the sealing surfaces in tightly clamping the membrane in position occurs on the softer rim surfaces, which thus acts somewhat in the manner of a gasket. Damage to the membrane or analytical side surfaces of the chamber, on clamping the parts together in sealing relationship, is thus minimized or avoided. Similarly the arrangement reduces the risk of rupture of the membrane when forming the domed structure therein in situ, and any surface damage or the like caused during this forming is taken by the softer material of the rim, i.e. the gasket, not by the foil membrane or the upper surface of the analytical side. The preferred flow valve according to the invention is of small scale, having a chamber which is generally circular as viewed in plan, the diameter thereof being from about 5-8 millimeters, the lateral extent of the membrane-engaging upper surfaces of the rim being from about 0.2-0.5 millimeters, and the rim height being from about 0.1-0.2 millimeters.

In practice, the side wall can be formed by a number of processes, such as chemically etching away a portion of the solid lower metallic surface in a pattern which leaves a rim of, the same, material of appropriate size and shape. Alternatively, recesses may be machined or chemically etched into the lower surface of the metal which will subsequently form the driver side of the chamber, and rings of appropriate material for forming the rims placed in or secured in such recesses. In another alternative, the under surface of the foil membrane, already electroplated or coated with material appropriate for forming the rims, may be etched away in a suitable pattern to leave a depending skirt thereon, which on assembly contacts the smooth, top surface of the driver side of the chamber. In a further alternative, the side wall of the driver side of the chamber may be formed from a thin sheet of soft metal such as copper or brass which is chemically etched or machined to form holes through the thickness of the sheet. A further etching or machining step can then be used to remove additional metal from the top surface of the copper or brass sheet, leaving raised rings of smaller surface area than the chamber surface area, which on assembly act as the sealing surface for the driver chamber. The lower wall of the driver chamber can then be constructed of a harder metal such as stainless steel, and may be polished to provide a smooth surface for the formation of the domed membrane. Most of these processes allows a highly polished finish to be applied to the major surfaces of the chamber on both the analytical side and the driver side, without the hindrance to the polishing operation of an obstructing rim.

The domed configuration is imparted to the membrane by deformation in situ, using fluid pressure. In this way, close conformity between the shaped membrane and chamber walls is achieved, for best operation of the membrane as a valve member The fluid pressure for forming the membrane to deform it is suitably supplied through the inlet or outlet port to the analytical side of the chamber. Further to improve the degree of conformity between the shaped membrane and the chamber, it is preferred to arrange to supply the fluid pressure for deformation through a port which is in opposition to a smooth surface portion of the driver side of the chamber. This reduces the risk of rupturing or deforming the sealing surface of the membrane.

The deformation and shaping of the membrane is suitably accomplished by applying a fluid pressure through the inlet or outlet port, after firm clamping together of the parts in sealing relationship, at pressures up to about 2,000 psi, for a few seconds. These conditions are appropriate for the aforementioned HAVAR membranes, and for most if not all foil membranes useful in the present invention. Normally an array of pairs of membranes assembled in chambers is formed at the same time, via a manifold from the fluid source. The valves are then ready for use. Any other methods for forming the membranes into domed shapes, such as pressing or stamping in an external apparatus, are unlikely to give the same degree of precision and conformity after assembly, as deformation in situ.

DETAILED DESCRIPTION OF THE SPECIFIC PREFERRED EMBODIMENT

With reference to FIG. 1 of the accompanying drawings, a valve design according to the invention comprises a chamber 10 of circular configuration as viewed in plan, and having a diameter of approximately 6.0 mm. The chamber is bounded at its upper extremity by a stainless steel block 12 having a highly polished undersurface 14 forming the analytical side of the chamber. The lower, driver side of the chamber 10 is formed of a copper block 16 which has an integral circular rim 18 upstanding therefrom and surrounding the chamber 10. The copper of rim 18 is softer than the stainless steel of block 12. An outlet port 20 extends through the block 12 to communicate with the chamber 10 at its center. An inlet port 22 also extends through the block 12 into the chamber 10, immediately adjacent to the rim 18. A driver gas inlet passageway 24 extends through the bottom wall 16 into the chamber 10 such that it enters chamber 10 adjacent to rim 18.

A foil membrane 26, of HAVAR, a high tensile strength alloy containing cobalt, chromium, nickel, and iron, of domed shape, is sealingly clamped at its periphery between the rim 18 and the undersurface 14 of block 12. In its full line position shown in FIG. 1, the membrane 26 provides free communication between outlet port 20 and inlet port 22 via chamber 10. In response to driver gas pressure provided through passageway 24, however, membrane 26 is movable to its broken line position as illustrated in FIG. 1, to close off communication between outlet port 20 and inlet port 22. The response speed of the membrane 26 to the driver gas pressure is very fast, of the order of a few milliseconds.

Figure 1A:
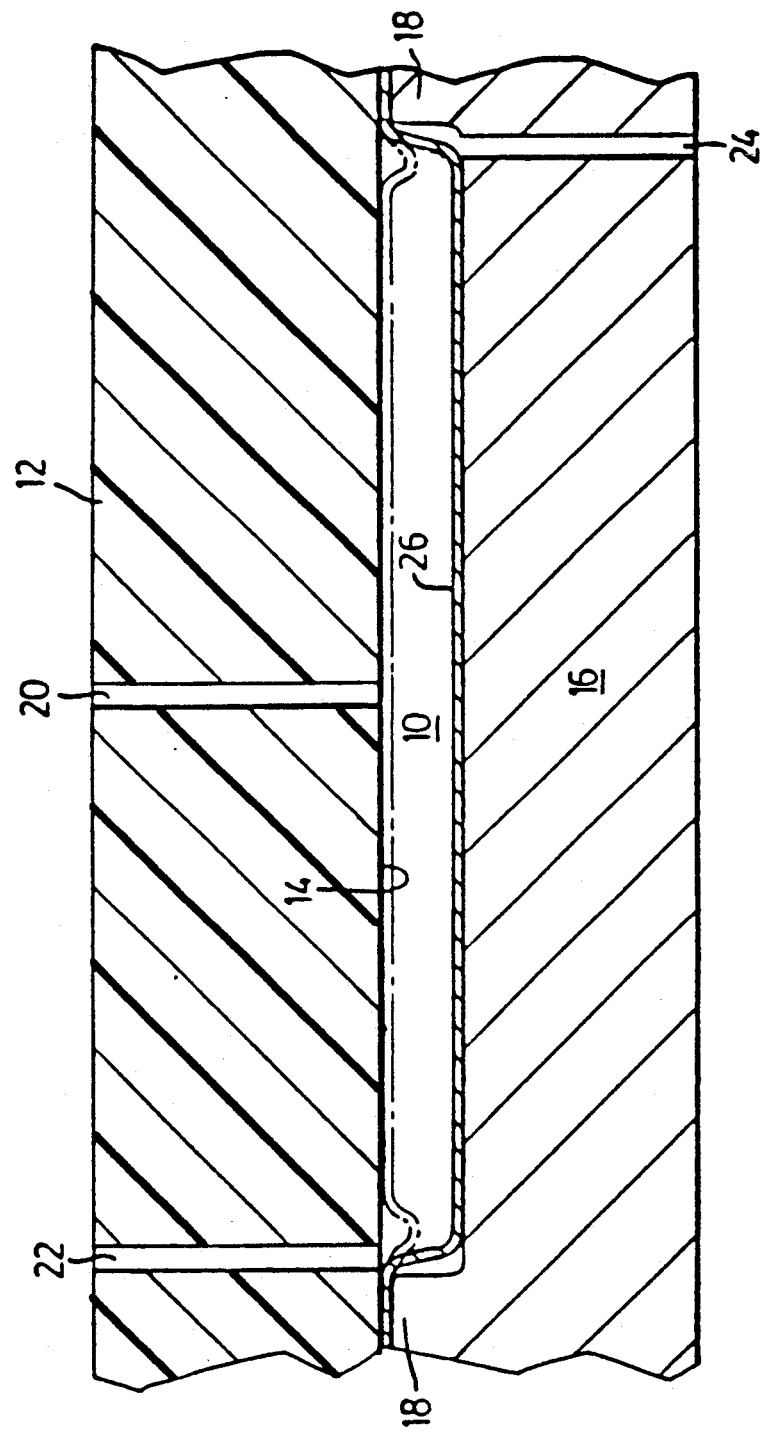
Figure 1B:
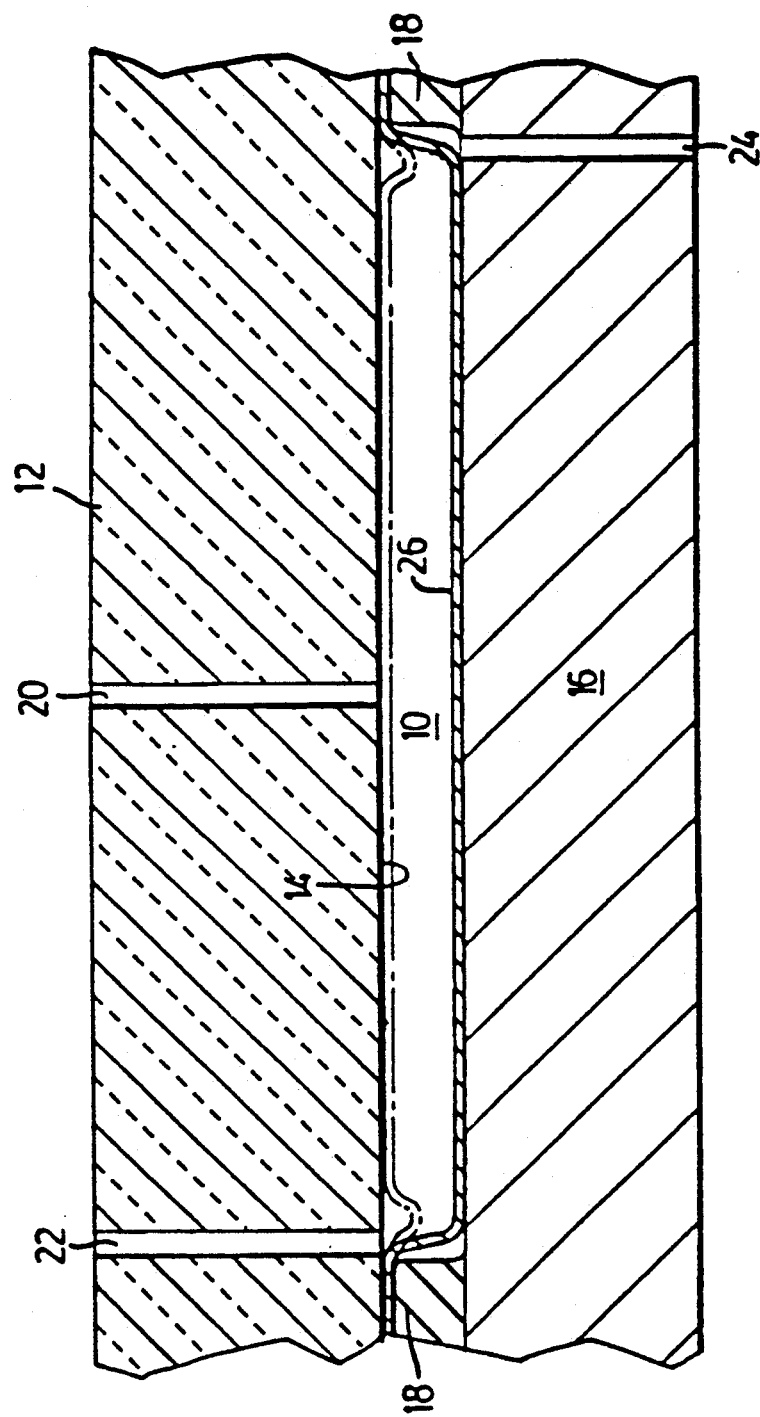
Figure 1C:
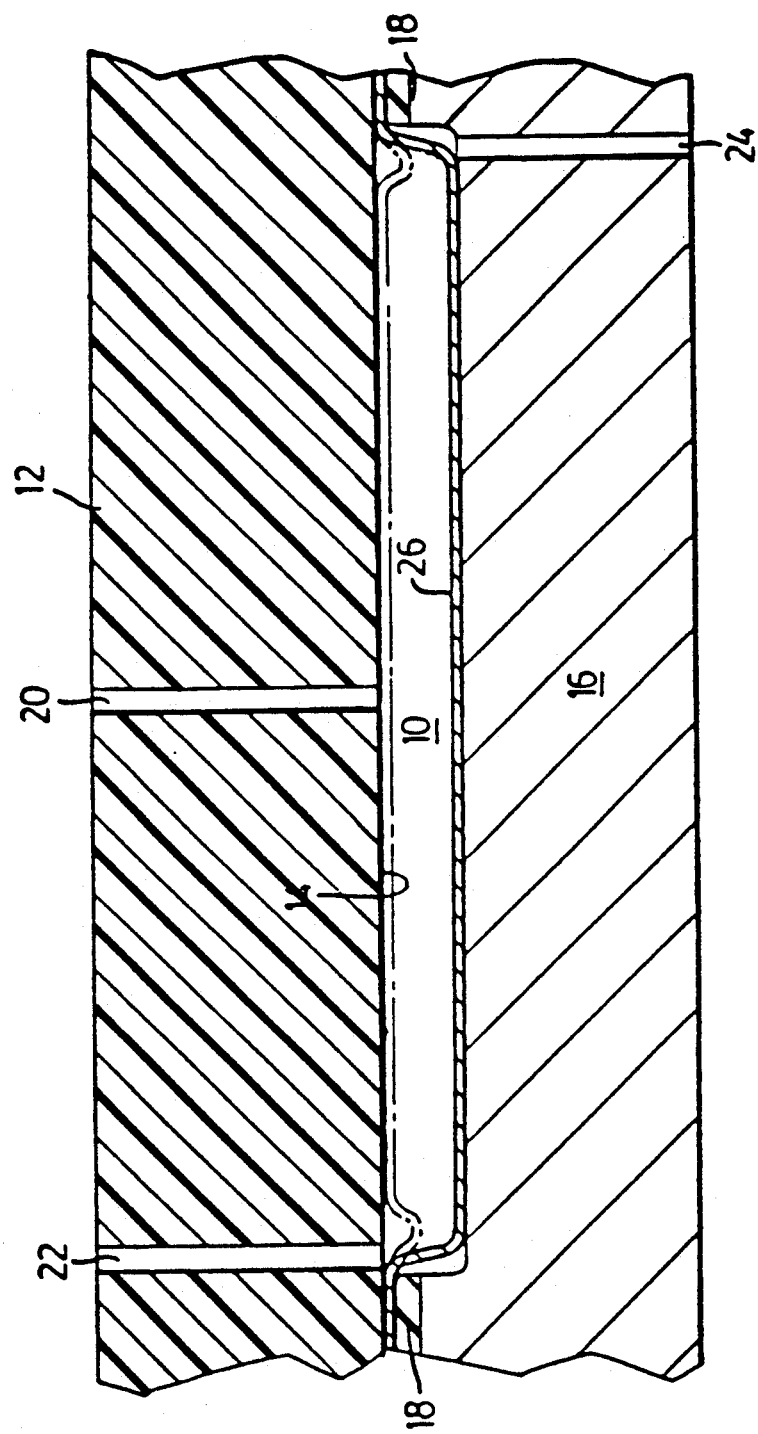

FIGS. 1A, 1B and 1C illustrate alternative embodiments similar to the one shown in FIG. 1. In FIG. 1A, the block 12 is made of a plastic coated with an inert metal on its undersurface 14, and in FIG. 1B block 12 is made of a ceramic material coated with an inert metal on its undersurface 14 and rim 18 is made of copper or brass secured to stainless steel bottom wall 16. In FIG. 1C, both the block 12 and the upper, membrane-engaging portion of the rim 18 are made of a plastic resin, undersurface 14 being coated with an inert metal. The materials shown in FIGS. 1, 1A, 1B and 1C for the block 12 and rim 18 can be used in various combinations other than those illustrated. For example, the stainless steel block 12 of FIG. 1 may be used with the plastic resin tipped rim 18 shown in FIG. 1C.

Figure 2:
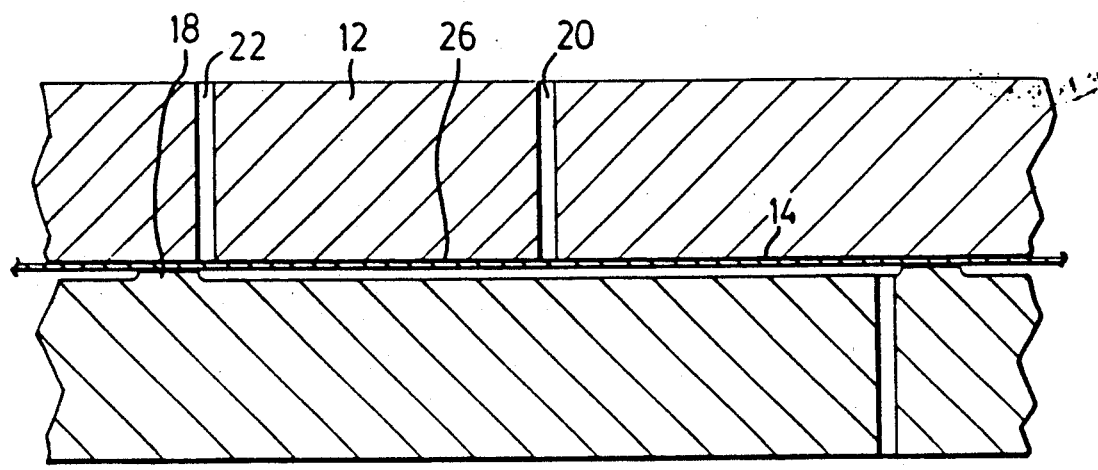
FIGS. 2, 3 and 4 are diagrammatic illustrations similar to FIG. 1, but with respective parts more closely to correct scale, showing the membrane shaping process as well as the operation of the valve.
Figure 3:
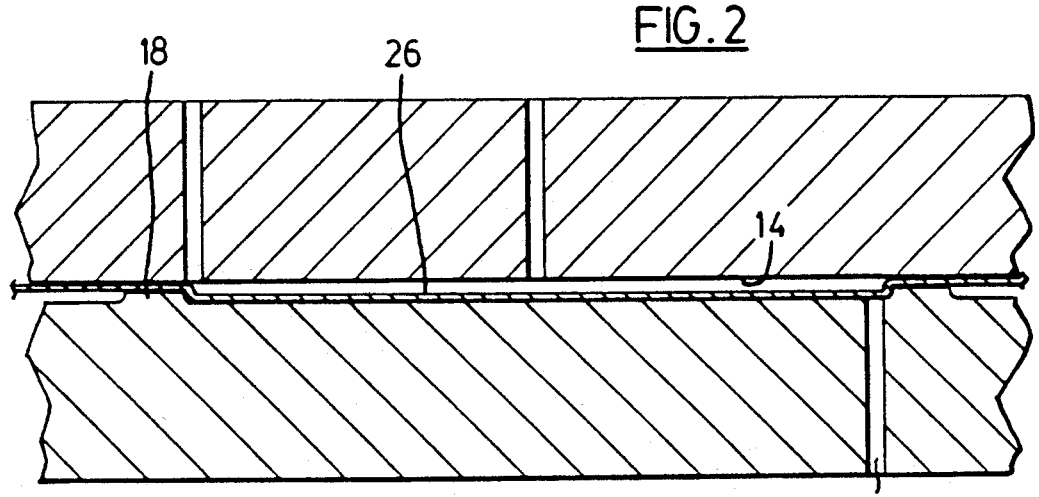

In FIG. 2 a valve arrangement as depicted in FIG. 1 is diagrammatically illustrated, prior to the deformation of the membrane 26 into its domed shape configuration shown in FIG. 1. Thus the membrane 26 is initially assembled and clamped between the rim 18 and top block 12 of the chamber, in a planar condition. When it is so placed, inlet port 22 is sealed, and high gas pressure is applied through outlet port 20 so that the membrane 26 is expanded and deformed into conformity with the driver side of chamber 10, i.e. into a dome shape, as illustrated in FIG. 3. The clamping seal between the upper surface of the rim 18 and the lower surface of the block 12 is sufficiently strong, due to the configuration of the rim as having a small top surface area, and due to the selection of relative hardness of materials, that the deformation takes place in a period of a few seconds, under a gas pressure of about 2,000 psi, to produce the required conformity. It will be noted that driver gas inlet passageway 24 is offset laterally from the exit from outlet port 20, so that the foil membrane does not take up an imprint of the unsupported floor of the chamber at a position opposite outlet port 20, since any such imprint might adversely affect the subsequent sealing of membrane 26 to close inlet port 20 when required.

Figure 4:
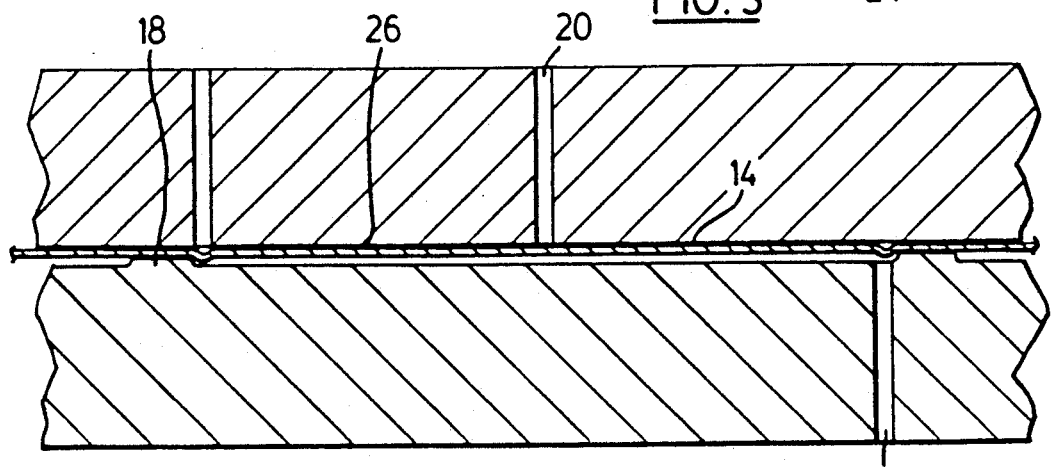

By this means, plastically deformed domed membrane 26 is produced, which is ready for operation in response to driver gas supplied through passageway 24, to move elastically to its closed position (FIG. 4) in which it seals against the upper surface 14 of block 12, to close off outlet port 20 as required. On release of the driver gas pressure, the membrane 26 relaxes to the position shown in FIG. 3, to allow the necessary free communication between outlet port 20 and inlet port 22.

Also in the arrangement shown in the drawings, and forming a further feature of the invention, the valve arrangement can be operated alternately using positive driver gas pressure and negative driver gas pressure. Negative pressure operation of this nature is advantageous in gas chromatography operations using such a small valve chamber, since it holds the dome shaped membrane in the open position, dramatically increasing the flow rates which can be obtained. Also, if it is desired to suck in a gas sample mixture for analysis using a pump working under negative pressure, a vacuum or negative pressure applied to the driver side of the membrane can be arranged to prevent collapse of the dome into the closed configuration shown in FIG. 4, rendering the valve unable to permit high flow rates. With most prior art valve arrangements utilizing such membranes, any attempts to suck in a gas sample mixture for analysis using a pump working under negative pressure will effectively severely reduce the flow or close the valve itself, rendering the sampling system inefficient or inoperable. In the process of the present invention, with the illustrated valve arrangement, however, an even greater negative pressure can be applied through the driver gas passageway 24 to the driver side of the membrane, to maintain the membrane 26 in its open position as illustrated in FIG. 3, during gas sampling with a pump operating under negative pressure, thereby permitting sufficient gas flow as required for chromatographic use.

Figure 5:
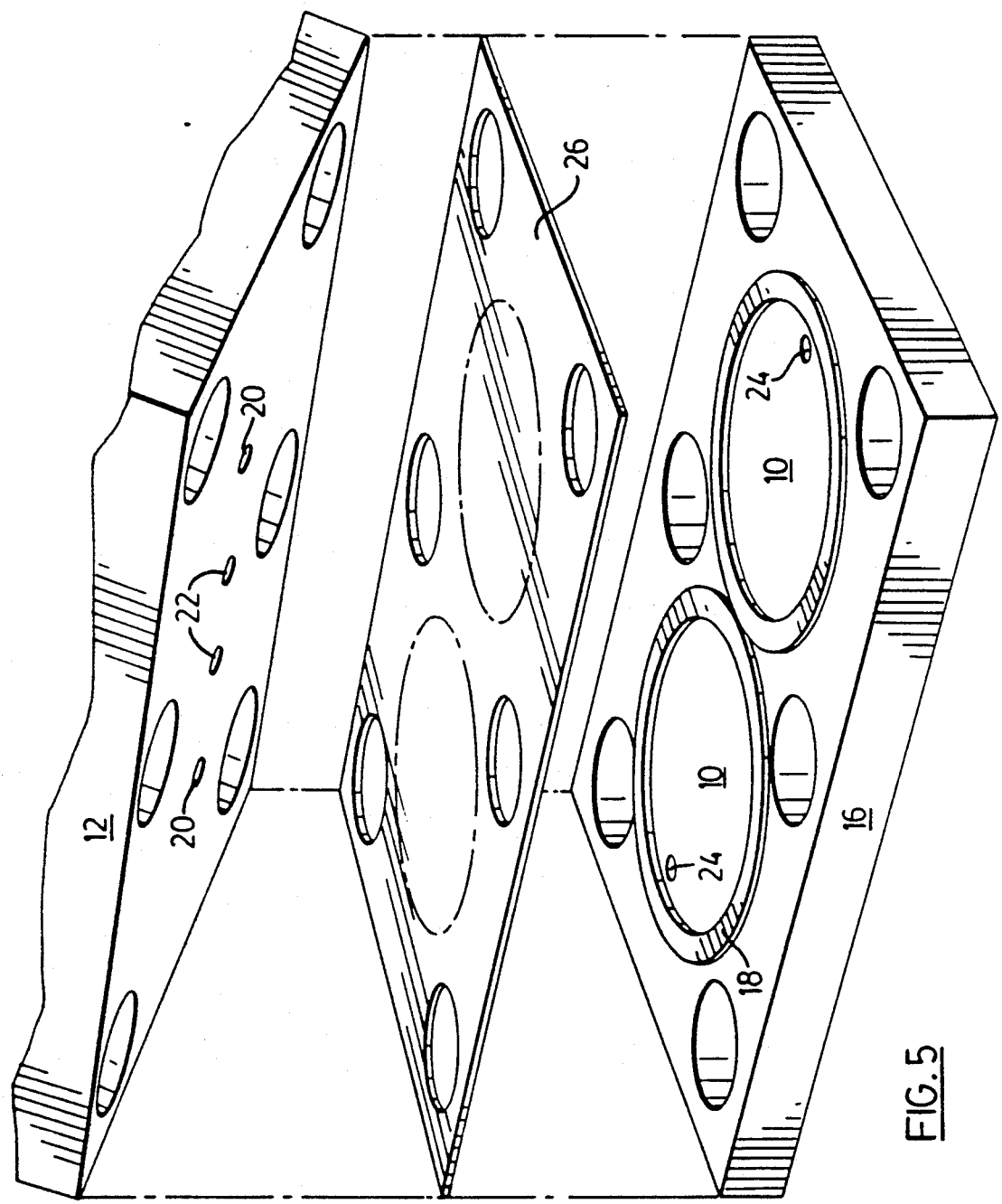
FIG. 5 is a diagrammatic exploded perspective view of a pair of valves operating according to the present invention, provided on a single metal block.
Figure 6:
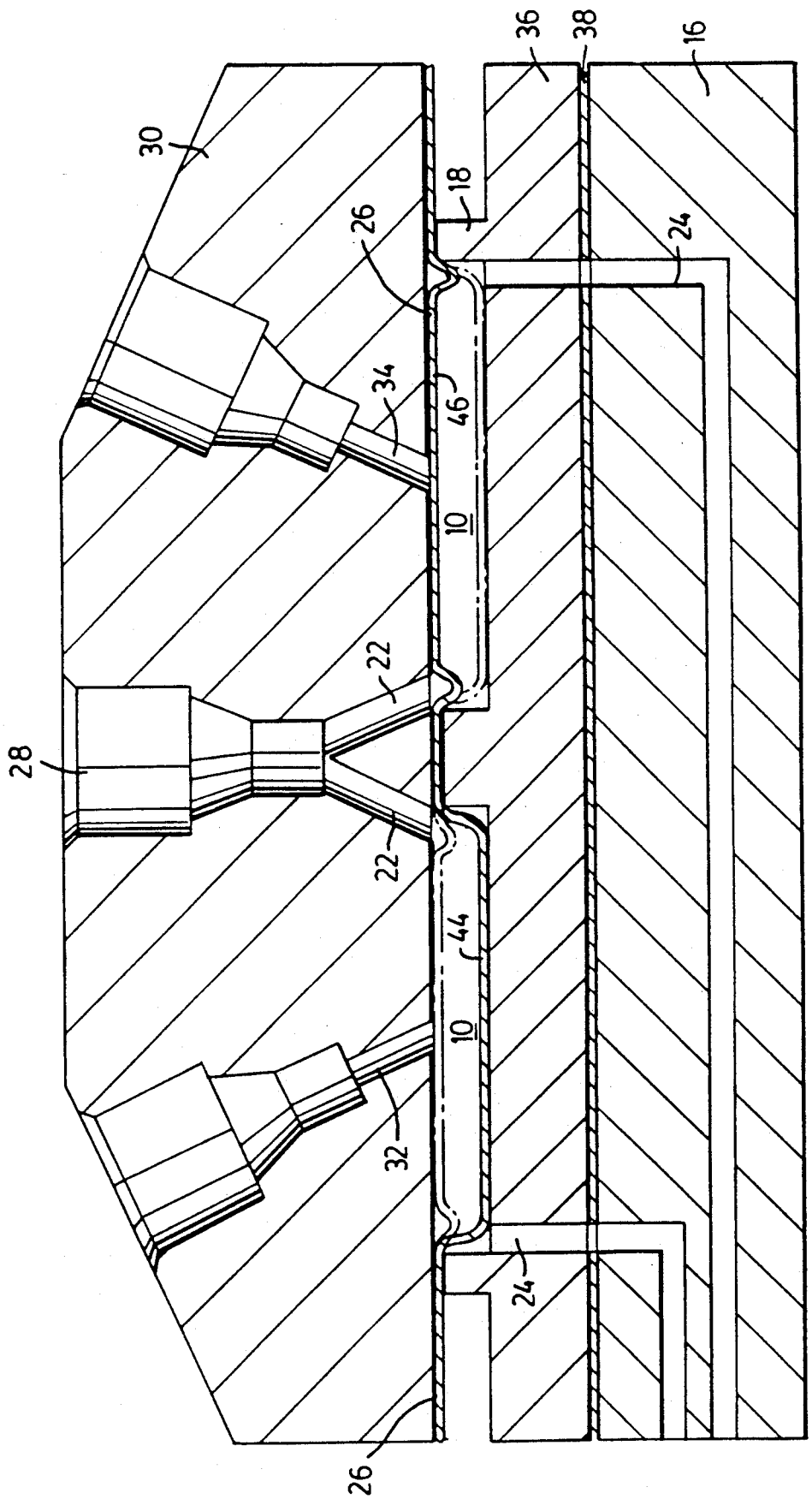
FIG. 6 is a diagrammatic cross section of a pair of interconnected valves according to this embodiment of the invention, in operative association with an analytical port block.)

FIG. 5 of the accompanying drawings illustrates in diagrammatic exploded perspective a pair of valve designs according to the invention, in a common upper stainless steel block 12 and a common lower copper block 16, in which a pair of rims 18 have been etched to define a pair of chambers 10. A metallic foil membrane 26 is formed for both valve arrangements from a single rectangular piece of the foil, with two domed configurations to register with the respective chambers 10. Driver gas ports 24 extend through the lower copper block 16 to enter the edge portions of each chamber 10 on the driver side. Outlet ports 20 extend through the top block 12 to register with the center of respective chambers 10. Inlet ports 22 extend from the respective inner peripheries of the chambers 10, through the upper block 12 to form a common, mutual inlet 28 (FIG. 6). The assembly in practice is bolted together by use of the bolt holes shown around the periphery of the component parts in FIG. 5.

Figure 8:
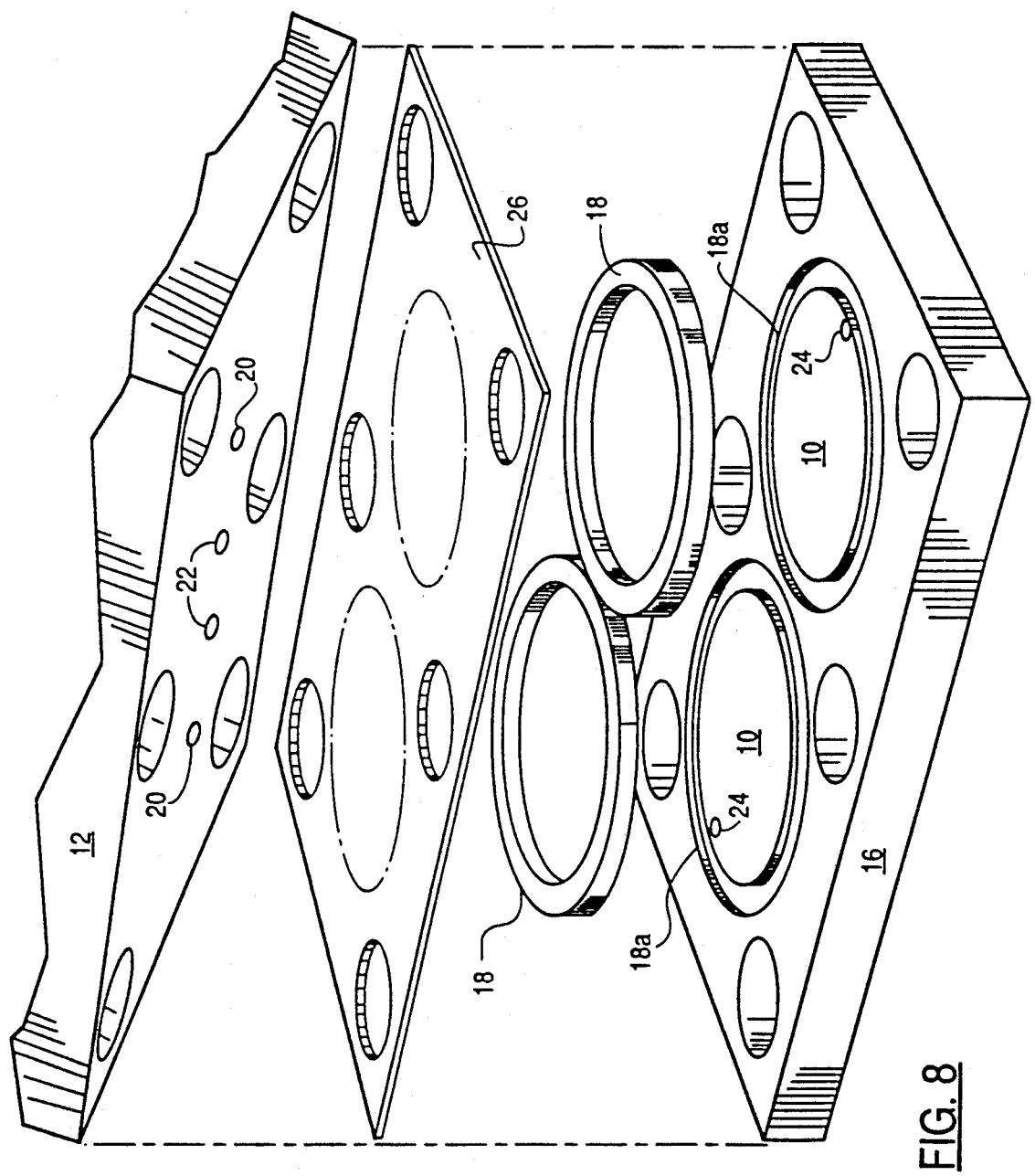
FIG. 8 illustrates a structure similar to that shown in FIG. 5 with the rims being separate rings which are seated in recessed formed on the top surface of the bottom wall.

FIG. 8 shows a structure similar to the one illustrated in FIG. 5, except that rims 18 are copper or brass rings which are seated in circular recesses 18a, machined in the upper surface of stainless steel drive section 16 and protrude upwardly therefrom.

FIG. 6 of the accompanying drawings shows the pair of valve arrangements as in FIG. 5, assembled with an analytical port block 30 which has a pair of outlets 32, 34 communicating with respective chambers 10, and a common, mutual inlet 28 in which the two independent inlet ports 22 from the respective chambers 10 are connected. The membrane 26 extending between and covering both of the chambers 10 is shown in full line in its relaxed, open position in the left hand chamber and in its closed position in the right hand chamber. It is shown in broken line in the reverse positions in each of the chambers. The lower stainless steel block 16 in this arrangement supports a copper gasket arrangement 36, with integral rims 18 defining the chambers 10 as previously described. The gasket formation is sealed in a gas-tight configuration to the lowermost stainless steel block 16 through the intermediary of a elastomeric pad 38. Inlet driver gas passageways are provided through lowermost block 16 and gasket arrangement 36, as shown at 24, for operation of the membrane 26 between its open and closed positions. Passageways 24 communicate through a pneumatic driver gas manifold, to solenoid actuated pneumatic driver valves (not shown).

The apparatus according to the invention is simple and straightforward to manufacture and operate, but nevertheless provides very small dead spaces in terms of internal valve volumes, which is advantageous for gas chromatography. It can be operated with high precision, over an extended number of cycles of operation, and at a wide variety of temperatures.

As mentioned above, and particularly with reference to FIG. 6, it will be seen that the apparatus can be operated advantageously using negative pressure applied to driver port 24 to hold the domed membrane portion 44 associated with outlet port 32 in the open position while the other domed membrane portion 46 is held closed against outlet port 34 by driver gas under positive pressure. A pump attached to outlet port 32 can then suck in, under negative pressure, a gas sample into a sample line with one end attached to inlet port 28 and the other end connected to the equivalent port in another valve arrangement similar to that of FIG. 6. Driver gas under pressure can then be applied to the driver port which was previously under negative pressure, to shut the domed membrane against outlet port 32 while the negative pressure is applied to driver port 24 to open the domed membrane associated with outlet port 34. Thus, the sample contained within the sample line can then be "switched" into the carrier gas flow for analysis.

It is merely necessary to ensure that the negative pressure applied to driver port 24 is at a lower value than the negative pressure produced by the pump causing the flow of gases through the associated analytical section of the valve, to ensure that its domed membrane remains in the open position. Such an operation under negative pressure provides sufficient sample gas flow for use in analytical gas chromatographic procedures.

Figure 7:
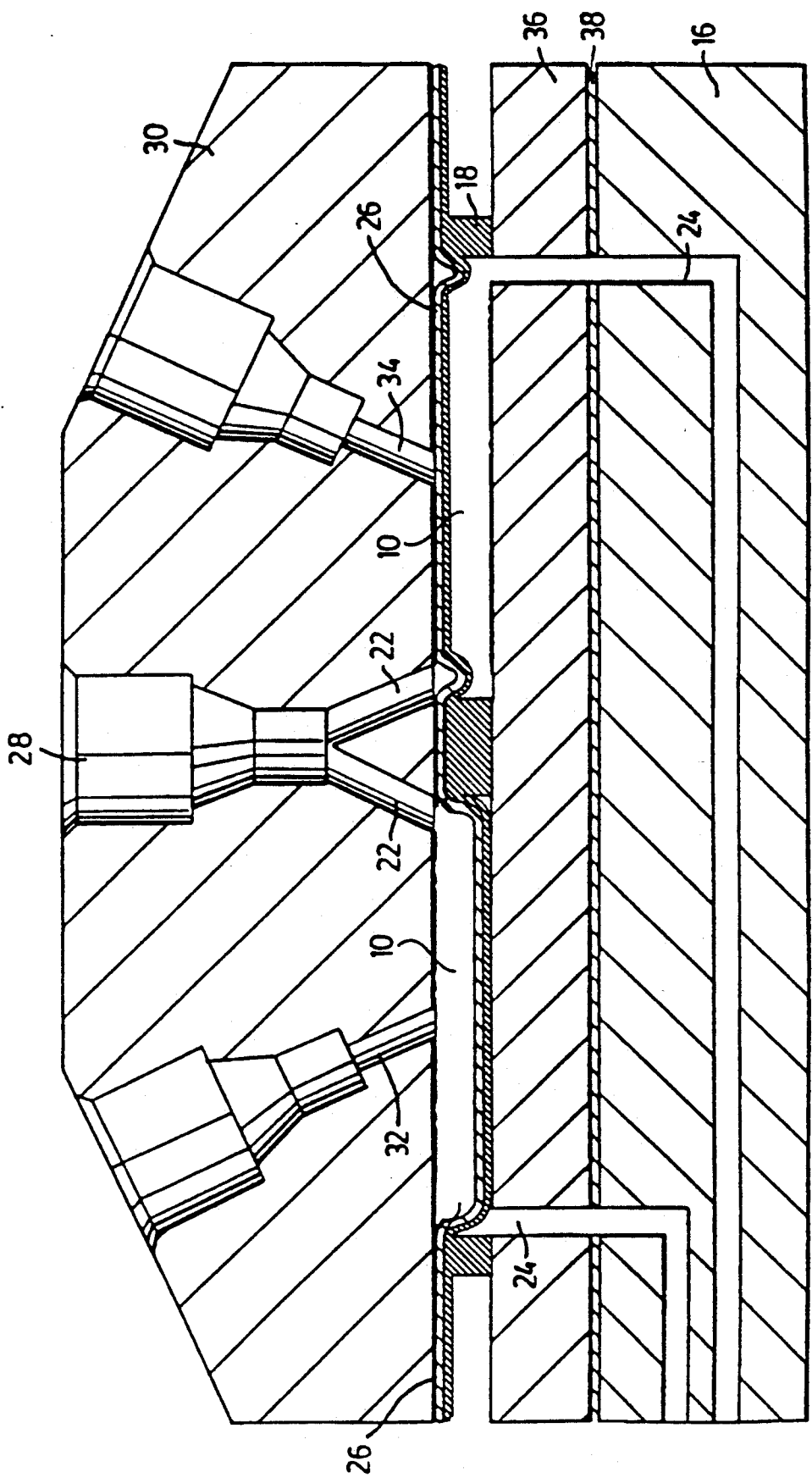
FIG. 7 illustrates a structure similar to that shown in FIG. 6, with the rim and membrane being integral.

FIG. 7 shows a structure similar to that illustrated in FIG. 6 except that membrane 26 is a cobalt-chromium-nickel alloy foil plated with copper or brass, etched on its lower surface to form rims 18 which are integral with membrane 26.

Whilst a specific preferred embodiment of the invention has been illustrated and described in detail herein, the invention is not to be interpreted as limited to any illustrated portion thereof. The scope of the invention is limited only by the scope of the appended claims.

What we claim is:

1. A fluid flow control valve comprising:
   a chamber divided into an analytical section and a driver section by means of a flexible, elastically operable membrane having metal surfaces to contact the fluid flow in the analuystic section;
   a smooth, continuous upper surface of metal defining the upper limit of the analytical section, a side rim surrounding the chamber and defining the periphery of the driver section of the chamber;
   at least one inlet port and at least one outlet port communicating with the analytical section of the chamber;
   a driver fluid port communicating with the driver section of the chamber; the metallic foil membrane being clamped in gas-tight engagement between the upper surface defining the upper limit of the analytical section and the upper edge of the side rim, and extending beyond the periphery of the side rim;
   the rim providing membrane-engaging upper surfaces of small surface areas compared with the surface area of the upper surface of the analytical section of the chamber;
   at least the upper, membrane-engaging portion of said rim being constituted of a material which is softer than the material of the membrane and softer than the material of the upper surface of the analytical section of the chamber, so as to deform the upper surface of the rim when the membrane is clamped into position.

2. The flow valve of claim 1 wherein the metallic foil membrane is constructed of inert metal.

3. The flow valve of claim 2 wherein the metallic foil membrane is constructed of high tensile strength metal foil.

4. The flow of claim 3 wherein metallic foil membrane is provided with a noble metal coating.

5. The flow valve of claim 4 wherein the membrane is made of cobalt-chromium-nickel alloy foil.

6. The flow valve of claim 5 wherein the membrane is provided with a noble metal coating.

7. The flow valve of claim 4 wherein the upper wall is of stainless steel and the upper, membrane-engaging portion of the rim is of plastic resin.

8. The flow valve of claim 3 wherein the upper wall of the analytical section is made of stainless steel and the upper, membrane-engaging portion of the rim is made of a material selected from the group consisting of brass and copper.

9. The flow valve of claim 3 wherein the upper wall of the analytical section is made of metal coated with an inert metal.

10. The flow valve of claim 3 wherein the upper wall of the analytical section is made of inert metal-coated plastic.

11. The flow valve of claim 3 wherein the upper wall of the analytical section is made of inert metal-coated ceramic.

12. The flow valve of claim 3 wherein the upper wall is of metal coated plastic and the upper, membrane-engaging portion of the rim is of plastic resin.

13. The flow valve of claim 3 wherein the upper wall is of metal coated ceramic and the upper membrane-engaging portion of the rim is of plastic resin.

14. The flow of claim 3 wherein the chamber is generally circular as viewed in plan, the diameter thereof being from about 5-8 millimeters, the lateral extent of the membrane-engaging upper surfaces of the rim being from about 0.2-0.5 millimeters, and the rim height being from 0.1-0.2 millimeters.

15. The flow valve of claim 14 wherein the driver section is formed of stainless steel and the rim thereof is a ring made of a material selected from the group consisting of brass and copper secured thereto.

16. The flow valve of claim 15 wherein the rim is formed from a ring made of a material selected from the group consisting of brass and copper seated in a circular recess in the upper stainless steel surface of the driver section and protruding upwardly therefrom.

17. The flow valve of claim 14 wherein the rim is a downwardly extending circular periphery integral with the membrane.

18. The flow of claim 17 wherein the membrane is formed of a cobalt-chromium-nickel alloy foil plated with a material selected from the group consisting of copper and brass, etched on its lower surface to provided said integral rim.

19. The flow valve of claim 1 wherein the operating, port-sealing portion of the metallic foil membrane is of domed configuration, adapted substantially to line the bottom of the chamber when in its open position, in substantial conformity therewith.

20. The flow valve of claim 19 wherein the analytical inlet port is laterally offset from the driver fluid inlet passage.

* * * * *